(12) United States Patent
Lemmon et al.

(10) Patent No.: US 6,818,134 B2
(45) Date of Patent: Nov. 16, 2004

(54) SYSTEMS AND METHODS FOR SCREENING AND OPTIMIZATION OF SOLID OXIDE FUEL CELL MATERIALS

(75) Inventors: John P. Lemmon, Schoharie, NY (US); Tracey Jordan, Schenectady, NY (US)

(73) Assignee: General Electric Company, Schenectady, NY (US)

(*) Notice: Subject to any disclaimer, the term of this patent is extended or adjusted under 35 U.S.C. 154(b) by 96 days.

(21) Appl. No.: 10/287,751

(22) Filed: Nov. 4, 2002

(65) Prior Publication Data

US 2004/0084374 A1 May 6, 2004

(51) Int. Cl.$^7$ .............................................. B01D 15/08
(52) U.S. Cl. ...................... 210/656; 210/198.2; 422/70; 427/115; 436/161
(58) Field of Search ............................. 210/656, 198.2; 422/70; 427/115, 421; 118/300, 301, 308; 366/177.1, 184; 436/161

(56) References Cited

U.S. PATENT DOCUMENTS

| | | | |
|---|---|---|---|
| 5,938,932 A | | 8/1999 | Connelly et al. |
| 6,090,280 A | | 7/2000 | Connelly et al. |
| 6,265,226 B1 | | 7/2001 | Petro et al. |
| 6,296,771 B1 | | 10/2001 | Miroslav |
| 6,569,518 B2 | * | 5/2003 | Yadav et al. ................ 428/323 |
| 2004/0062142 A1 | * | 4/2004 | Wei et al. ................ 366/177.1 |
| 2004/0068865 A1 | * | 4/2004 | Lemmon et al. ............... 29/746 |
| 2004/0086633 A1 | * | 5/2004 | Lemmon et al. ............. 427/115 |

FOREIGN PATENT DOCUMENTS

| | | |
|---|---|---|
| EP | 0 453 107 B1 | 1/1995 |
| EP | 1 193 496 A | 3/2002 |
| WO | WO 02/056420 A2 | 7/2002 |

OTHER PUBLICATIONS

Patent Abstract of Japan Publication No. 06308086 Dated Apr. 11, 1994.

Somsen et al. "Spray jet assembly interface for the coupling of reversed–phase narrow–bore liquid chromatography and Fourier transform spectrometry" Journal of Chromatography, Elsevier Science Publishers B.V. Amsterdam, NL, vol. 552 Nos. 1/2. Aug. 9, 1991 pp. 635–647.

International Search Report for Application No. 03256866.9–2119–Dated Feb. 16, 2004.

* cited by examiner

Primary Examiner—Ernest G. Therkorn
(74) Attorney, Agent, or Firm—Cantor Colburn LLP

(57) ABSTRACT

Systems and methods for high-throughput fabrication and evaluation of electrode and electrolyte material performance for solid oxide fuel cells. A system comprising a substrate, an auto-sampler operable for simultaneously controlling the flow rates of 2 or more solid oxide fuel cell components, a delivery apparatus, a mass flow controller, an x-y motion stage, and a microprocessor operable for controlling the system. A method comprising providing a library of samples, continuously and controllably supplying desired amounts of the samples to a liquid chromatography system where a multi-compositional mixture is formed, serially loading the multi-compositional mixture into a common sprayer, serially and distributively spraying the multi-compositional mixture onto a surface of a substrate, forming a discrete or continuous gradient array of the mixture reacted on the substrate, and evaluating the performance of the mixture for use in solid oxide fuel cells.

12 Claims, 1 Drawing Sheet

SYSTEMS AND METHODS FOR SCREENING AND OPTIMIZATION OF SOLID OXIDE FUEL CELL MATERIALS

CROSS-REFERENCE TO RELATED APPLICATIONS

United States Utility Patent Application by Lemmon et al., entitled "Systems And Methods For The Fabrication Of Solid Oxide Fuel Cell Components Using Liquid Spraying" filed the same day as the present Application is hereby incorporated by reference.

BACKGROUND OF THE INVENTION

1. Field of the Invention

The present invention relates generally to the field of liquid chromatography. More particularly, the present invention relates to high throughput systems and methods for the fabrication and measurement of solid oxide fuel cell components using a modified liquid chromatography instrument.

2. Description of the Related Art

A fuel cell is an energy conversion device capable of generating electricity and heat by electrochemically combining a gaseous fuel and an oxidizing gas via an ion-conducting electrolyte. The defining characteristic of a fuel cell is the ability to convert chemical energy directly into electrical energy without the need for combustion, giving much higher conversion efficiencies as compared to conventional methods. A fuel cell is mainly composed of an electrolyte and two electrodes, the anode and the cathode. The classification of fuel cells is generally done according to the nature of the electrolyte.

The electrolyte is operable for preventing the two electrodes from coming into electronic contact while allowing a flow of charged ions generated at the cathode to pass through it in order to be discharged at the anode. The nature of the electrolyte determines the operating temperature of the fuel cell. The function of the electrode is to bring about a reaction between the reactant (fuel) and the electrolyte, without itself being consumed or corroded. It must also, by definition, be an electronic conductor and bring the phases into contact.

There are many different types of fuel cells, and several parameters may vary depending on what the fuel cell is used for. For example, solid oxide fuel cells (SOFCs) are fuel cells constructed entirely from solid-state materials. SOFCs use an ion-conducting oxide ceramic as the electrolyte, and are operated in the range of about 900° C. to about 1000° C. SOFCs provide several advantages compared to other fuel cell types, such as generating few problems with electrolyte management and having the highest efficiencies of all fuel cells (approximately 50–60%). SOFCs may be used in large-scale power generation, distributed power and vehicular applications.

One of the key challenges in developing a SOFC is developing high-performance electrode and electrolyte materials that meet SOFC performance and cost requirements. While there are lists of potential candidate materials for both electrodes and electrolytes, significant efforts are required to optimize material combinations, chemical compositions, processing conditions and the like. This is especially true as the vast majority of such potential candidate materials are either ternary or quaternary-based.

For example, yttrium-stabilized zirconium (YSZ) is commonly used as an electrolyte material in SOFCs. However, electrolyte performance is relatively sensitive to the ratio of Y to Zr, and this component ratio must be carefully optimized. The same is true for other potential candidate materials for electrolytes, including Sr-doped $CeO_2$, CGO, and the like. Electrode material composition is also critical to the performance of a SOFC. For example, the composition of $La_xSr_{1-x}MnO$ (3-d) (LSM), a common cathode material, may greatly affect its electrical conductivity and electrochemical activity.

Typically, various combinations of elements or components with varying chemical compositions are individually formulated and tested in order to achieve optimal performance for electrode and electrolyte materials, a relatively slow, labor-intensive, and costly process. Thus, what are needed are high-throughput systems and methods that make SOFC-related material development more efficient. The systems and methods of the present invention use a combinatorial or small-scale approach to achieve the high-throughput fabrication, evaluation and optimization of electrode and electrolyte materials for use in SOFCs.

Likewise, although SOFCs are a promising technology for producing electrical energy from fuel with relatively high efficiency and low emissions, barriers to the widespread commercial use of SOFCs include their relatively high manufacturing cost and high operating temperatures. The manufacturing cost is driven primarily by the need for state of the art, electrolyte-supported fuel cells capable of operating at relatively high temperatures (approximately 1000° C.). Manufacturing costs may be substantially reduced if the operating temperature could be lowered to below 800° C., allowing the use of less expensive structural components, such as stainless steel. A lower operating temperature would also ensure a greater overall system efficiency and a reduction in the thermal stresses in the active ceramic structures, leading to longer life expectancies.

One of the barriers to a reduction in the operating temperature of SOFCs is the efficiency of the common cathode material, LSM. At intermediate temperatures, the cathodic polarization of LSM is relatively high, leading to large efficiency losses. Thus, new cathode compositions with lower activation polarizations are needed. However, standard ceramic processing techniques for fabricating new cathode compositions are time consuming and costly. Typically, new powder compositions are synthesized in a plurality of steps, including precipitation, filtration, and calcining. Because the microstructure (i.e., the porosity) of the cathode structure contributes substantially to its performance, careful processing of the powder must be performed in order to produce cathode structures with uniform microstructures. The expense associated with synthesizing such ceramic powders limits the number of cathode compositions that may be fabricated and evaluated.

Thus, what is needed are high-throughput systems and methods for the fabrication and evaluation of electrolyte and electrode material performance for solid oxide fuel cells. Further, what is needed are systems and methods to synthesize and optimize the performance of electrode and electrolyte combinations. Still further, what is needed are small scale techniques to optimize these materials based on chemical composition and variable processing. Rapid device performance methods coupled with structural and surface methods would allow for an increased discovery rate of new materials for SOFCs.

BRIEF SUMMARY OF THE INVENTION

In various embodiments, the present invention provides high-throughput systems and methods for the fabrication and evaluation of electrode and electrolyte materials for use in solid oxide fuel cells ("SOFCs"). The present invention comprises systems and methods for synthesizing, evaluating, and optimizing the performance of such electrodes and electrode-electrolyte combinations and uses small-scale techniques to perform such synthesis, evaluation and optimization based on variable chemical composition and processing. Advantageously, rapid device performance systems and methods coupled with structural and surface systems and methods allow for increased rates of discovery for new materials and material combinations for use in SOFCs.

In various embodiments, the present invention provides facile and rapid techniques for synthesizing multi-compositional inorganic materials generally. These techniques may be used to discover new inorganic materials for use in SOFCs (such as electrodes, electrolytes, interconnects, seals, and the like), phosphors, scintillators, PZT materials, and the like. The techniques allow for the synthesis and analysis of gradient or spatially resolved compositions that may be used to offset non-steady-state applications.

In one embodiment of the present invention, a method for the fabrication and evaluation of an array of electrode or electrolyte materials for use in SOFCs comprises providing a plurality of materials suitable for delivery to the surface of a substrate. As described above, the plurality of materials may form a gradient coating in the form of a gradient array on the surface of the substrate or, alternatively, they may infiltrate the substrate, forming an array of electrode or electrolyte materials suitable for evaluation. The plurality of materials may form the array of electrode or electrolyte materials by selectively altering the chemical composition and/or physical microstructure of each of a plurality of regions of the substrate.

In another embodiment, for example, a plurality of components are mixed in tubes of a liquid chromatography (LC) instrument. Any number of components may be added and a gradient flow of the components may be accomplished using LC software. In yet another embodiment, the gradient flow is formed as previously described, but after the various components are delivered to the substrate 106, a processing step is carried out which allows or causes the components to interact to form layers, blends, mixtures, and/or materials resulting from a reaction between components. In a further embodiment, two or more components may be delivered to predefined regions on the substrate using a parallel delivery technique, such that the components interact with each other before contacting the substrate 106. Each component may be delivered in either a uniform or gradient fashion to produce either a single stoichiometry or, alternatively, a large number of stoichiometries within a single predefined region.

With the synthesis of materials for SOFCs, both chemical composition and microstructure are important variables. Producing a gradient flow using the methods and systems of the present invention promotes the replication of compositional libraries, thus opportunities for processing with multiple variables and microstructure control are feasible. Replication of the arrays allows for the investigation of multi-processing variables. The individual compositions in a given array may be tested for conductivity and for catalytic activity in the presence of oxygen by monitoring the over-potential at various temperatures using a multi-probe instrument. Subsequent results allow for the ranking of composition and processing based on performance measurements.

In a still further embodiment, the present invention provides a system for the fabrication and evaluation of a gradient mixture of solid oxide fuel cell components. The system comprises a substrate, a liquid chromatography instrument operable for simultaneously and continuously controlling 2 or more solution flow rates, an injection system operable for serially and distributively injecting samples selected from a sample library into the gradient mixture to form a multi-compositional material, and a delivery device operable for delivering the gradient mixture to the substrate.

In a still further embodiment, the system further comprises an x-y motion stage connected to the delivery device, the substrate or both, wherein motion of the x-y stage is coordinated with the delivery of the gradient mixture to the substrate, a mask operable for creating discrete or continuous gradient compositions, a shutter operable for selectively allowing/preventing the mixture from being sprayed onto the substrate by opening/closing, and a general purpose processor operable for controlling functions of at least one of the following: the liquid chromatography instrument, the injection system, the delivery device, the x-y motion stage, the mask, the shutter, and the temperature controlled heating block.

In a still further embodiment, the present invention provides a system comprising a substrate, an auto-sampler operable for simultaneously controlling the flow rates of 2 or more solid oxide fuel cell components, and wherein the auto-sampler is further operable for serially and distributively injecting samples selected from a sample library into a gradient mixture to form a multi-compositional material, a delivery apparatus operable for delivery the gradient mixture to the substrate, a mass flow controller operable for controlling the flow of the gradient mixture to the substrate, an x-y motion stage attached to either the substrate of the delivery apparatus, an a microprocessor for controlling the function of the auto-sampler, the delivery apparatus, the mass flow controller and the x-y motion stage.

In a still further embodiment, the present invention provides a method for the fabrication and evaluation of electrode and electrolyte material performance for solid oxide fuel cells. The method comprises providing a library of samples comprising electrode materials, electrolyte materials, metals, non-metals, soluble metal salts, organic binders, polymers, and any other components used to produce the solid oxide fuel cells, continuously and controllably supplying desired amounts of the samples to a liquid chromatography system where a multi-compositional mixture is formed, serially loading the multi-compositional mixture into a common sprayer, serially and distributively spraying the multi-compositional mixture onto a surface of a substrate using a spraying apparatus, forming a discrete or continuous gradient array of the mixture reacted on the substrate, and evaluating the performance of the mixture for use in solid oxide fuel cells.

BRIEF DESCRIPTION OF THE DRAWINGS

A variety of specific embodiments of this invention will now be illustrated with reference to the Figures. In these Figures, like elements have been given like numerals.

DETAILED DESCRIPTION OF THE INVENTION

Figure 1:
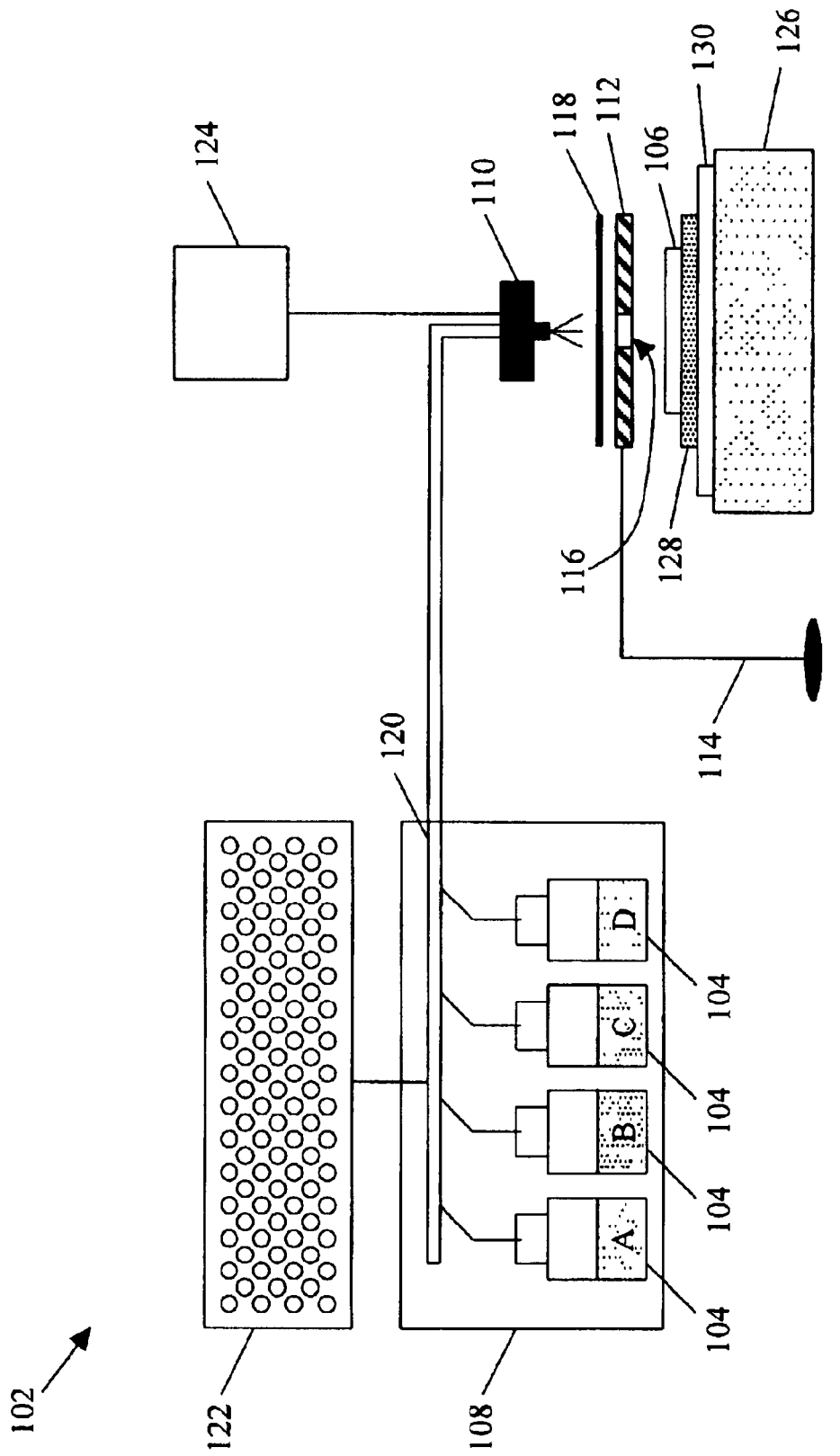
FIG. 1 is a schematic diagram of a liquid chromatography (LC) system for studying SOFC components in accordance with an exemplary embodiment of the present invention.

As required, detailed embodiments of the present invention are disclosed herein, however, it is to be understood that the disclosed embodiments are merely exemplary of the invention that may be embodied in various and alternative forms. Specific structural and functional details disclosed herein are not to be interpreted as limiting, but merely as a basis for the claims as a representative basis for teaching one skilled in the art to variously employ the present invention. Throughout the drawings, like elements are given like numerals. The methods and systems described below apply to solid oxide fuel cell materials, however, in principle also apply to any high throughput screening technique employing liquid chromatography instrumentation or the like.

In various embodiments, the systems and methods of the present invention are based on the nebulization into a hydrogen flame or the nebulization of soluble metal salt mixtures, small organic or polymer solutions to form discreet or continuous gradient arrays of materials reacted on, with or within a substrate. A compositional gradient is formed using a liquid chromatography instrument (LC) in which 2 or more solution flow rates may be simultaneously controlled. This provides the capability to control the amount and ratios of soluble metal salts that form the bulk of a material and allows for a wide range of compositions to be produced continuously. An auto-sampler of the LC instrument may be utilized to inject mixtures of other components, metal and nonmetal, into the gradient flow to form a multi-compositional material. Additional components may enhance a physical or chemical property, such as electrical or ionic conductivity, pore size and pore density. The facile rapid method for making SOFC materials with the methods and systems of the present invention promote the replication of compositional libraries, thus the opportunity for processing with multiple variables and allowing another dimension towards microstructure control.

With reference to FIG. 1, in one embodiment of the present invention, a LC system 102 for the fabrication of a compositional gradient of electrode and electrolyte materials for use in SOFCs comprises a plurality of materials 104 (materials A, B, C and D are shown) suitable for delivery to the surface of a sample substrate 106. The plurality of materials 104 may form either a discrete or a continuous gradient array of materials acted on, with or within the reactive or unreactive substrate 106. The compositional array is formed using a LC instrument 108 in which 2 or more solution flow rates (4 are shown) are simultaneously controlled.

The substrate 106 may be a material having a rigid or semi-rigid surface. In several embodiments, at least one surface of the substrate 106 will be substantially flat. The substrate may be reactive or unreactive, and porous or nonporous. The substrate 106 may comprise physical separations between testing regions for different SOFC materials. The substrate 106 may comprise, for example, porous or dense yttrium-stabilized zirconium ("YSZ"), a green ceramic, a plastic coated ceramic, a platinum metal, or the like. The surface area of the substrate is designed to meet the requirements of a particular application. Preferably, the surface area of the substrate 106 is in the range of 1 $cm^2$ to 50 $cm^2$, more preferably, in the range of 30 $cm^2$ to 40 $cm^2$. For the evaluation of electrode materials for use in SOFCs, a Fe—Cr alloy or a conductive ceramic, such as LaCrO3 or platinum metal, may be used for the array electrodes. For the evaluation of electrolyte materials for use in SOFCs, a LaxSr1-xMnO (3-d) ("LSM")-coated Fe—Cr alloy, platinum metal, or LaCrO3 may be used for the array electrodes.

A predetermined region on the substrate is a localized area that is, was, or is intended to be used for the deposition of a specific solid oxide fuel cell mixture. The predetermined region may have any convenient shape, e.g., linear, circular, rectangular, elliptical or wedge-shaped. The region may be identified with a marker, such as a tag or bar code that may be used to identify which mixtures are deposited onto which predetermined region on the substrate 106. The surface area, number of regions and locations of the predetermined regions may depend on the particular application.

The LC instrument 108 operable for delivering component mixtures to the surface of the substrate is positioned above or adjacent to the surface of the substrate 106. To form the solid materials, the liquid mixture may be aerosolized using an ultrasonic nebulizer 110 or electrostatic forces, and sprayed onto a heated substrate 106. In various embodiments, a nebulizer or sprayer, plain, plasma, hydrogen flame sprayer, or any other liquid sprayer known in the art may be used. The sprayer may include a delivery device, such as a syringe, pipette, microdispenser, liquid coating device, spin coating device, dip coating device, elongate coating head, powder coating device, vapor coating device, infiltration device or any other dispensing or coating device known to those of ordinary skill in the art. The ultrasonic nebulizer 110 is arranged in such a way, as is illustrated in FIG. 1 for example, such that a discrete or continuous gradient array of materials is created. In one embodiment, a gradient array is formed using a hydrogen flame as the deposition method. Preferably, the ultrasonic nebulizer 110 is movable relative to the surface of the substrate 106, such that the one or more mixtures may be delivered to specific predetermined regions of the surface of the substrate 106. Optionally, these predetermined regions may correspond to the locations of a plurality of holes or openings of a mask 112. The mixture of materials deposited onto the substrate 106 forms the array 102 of SOFC components.

Generally, physical masking systems may be employed in combination with various deposition techniques in order to apply components onto the substrate 106 in a combinatorial fashion, thereby creating arrays of resulting materials at predetermined locations on the substrate 106. The arrays of component materials will usually differ in thickness across the substrate 106. The components can, for example, be dispensed to the substrate 106 in the form of a gas, a liquid or a powder. Additionally, such dispensing systems may be manual or, alternatively, may be automated using, for example, robotics techniques. The substrate 106 may be disposed underneath and adjacent to the mask 112. Typically, the mask 112 comprises a plate, sheet, film, coating or the like supported by a holder 114. The mask may not be a necessary component of the system if a gradient is known. The mask comprises one or more holes 116 disposed therethrough or openings disposed therein. In one example, a hole may have a diameter of about 1 mm. Each of the one or more holes 116 or openings may be, for example, substantially circular, oblong, square, rectangular, triangular or a more complex shape. The mask 112 is disposed adjacent to a surface of the substrate 106 such that material passing through each of the plurality of holes is selectively prevented or shielded from contacting predetermined regions of the surface of the substrate 106. A shutter 118 may be disposed between the ultrasonic nebulizer 110 and mask 112. The shutter is a mechanical device that selectively allows/prevents a mixture from being sprayed on to the substrate 106 by opening/closing.

Predetermined combinations of materials (e.g. A, B, C and D) are mixed in the LC instrument 108 prior to the actual dispensing or delivery. Mixing may take place within a plurality of tubes 120 of the LC instrument 108 (1 tube is illustrated in FIG. 1). Prior to being delivered to the surface of the substrate 106, the plurality of materials 104, or precursor components, may be mixed in the plurality of tubes or mixed using a mixing device. The mixing device may include one or more tubes incorporating one or more baffles, a variable-speed rotary mixer, a screw mixer, a sonic mixer or the like.

According to one embodiment, with reference to FIG. 1, the LC system 102 of the present invention comprises a sample injection system 122, such as an auto-sampler, for serially and distributively injecting samples selected from a sample library, into the gradient flow to form a multi-compositional material. The auto-sampler may be used to inject mixtures of metals, non-metals, organic binders and polymers for structural variation. Pre-mixed vials may contain matters or polymers that doped in to study the effect on the gradient. With reference to FIG. 1, approximately 100 samples are shown, however, the injection system 122 may be of various design and configuration and may comprise any number of samples. The injection system 122 may comprise an array of wells or sample vials. The flow rates of the samples are simultaneously controlled. This provides the capability to control the amount and ratios of bulk components as well as other components that form the residual of the mixture. The sample injection system 122 may comprise an injector and a multi-port switching valve. The injector provides a motive force for injecting a sample under pressure through the multi-port switching valve into the mixing tubes 120 and the gradient flow being supplied to the ultrasonic nebulizer 110, or other sprayer. The multi-port switching valve provides sequential distribution of the samples to the gradient flow. The injector and multi-port switching valve may be separate components or a single component.

Sample injection into the gradient flow may be done so in any manner known in the art. Samples may also be subject to preparation steps prior to being injected. Preparation steps may include heating, cooling and mixing with other samples prior to injection. In one example, only one sample is drawn into the injector at a time. The one sample is injected into the gradient flow before drawing the next sample into the injector. In a second example, however, two or more samples may be drawn into the injector sequentially and allowed to mix, such that the two or more samples reside in the injector at the same time. The flexibility of the injection system 122 provides for any variety of sample combinations and the rapid introduction of the one or more samples into the gradient flow.

The injection system 122 may be manually or automatically controlled. For example, a metal sample may be drawn from the sample library manually with a syringe-type instrument and manually delivered to the tubes 120 containing the gradient flow. In an automatic system, some function of the system is performed automatically, such as sample selection or delivery. Solvent concentrations may be programmed to increase, hold steady, go down or any other function. Preferably, in order to rapidly and accurately select samples and proper measurements, the samples are drawn from their respective vials and delivered in a fully automated manner, such as with an auto-sampler. A microprocessor of the auto-sampler may be programmed to direct the auto-sampler to withdraw a sample from a sample vial into the injector, and then direct the injector to a port for injecting the sample into the gradient flow tube 120. In one embodiment, the auto-sampler may be programmed to automatically sample each vial of the library of samples in an ordered fashion. Preferably, the microprocessor of the auto-sampler comprises a user-interface that may be programmed to allow for various sampling protocols. The auto-sampler may also be controlled manually.

Solution flow rates of 2 or more solutions may be simultaneously controlled using a mass flow controller 124. The solution flow rates may be controlled using metering pumps located in the LC instrumentation. Any gas for nebulization, reaction, and flame may be controlled by the mass flow controller 124. The mass flow controller 124 provides the capability to control the amount and ratios of soluble metal salts that form the bulk of a material, as well as materials from the injection system 122 that make up the residual. Further, the mass flow controller 124 allows for a wide range of compositions to be produced continuously.

Preferably, the ultrasonic nebulizer 110 is movable relative to the surface of the substrate 106, either via movement of the nebulizer 110 or via movement of the substrate 106, such as through the use of a programmable x-y stage 126 or the like. A continuous compositional gradient may be created by applying different feed rates to 2 or more metal containing solutions and simultaneously moving the target in either the x or y direction. The continuous gradient can be captured spatially by using the x-y motion stage 126 and coordinating the flow with the rate of motion. Discrete compositions may be created by the interruption of the flow coordinated with the x-y stage 126. This may be accomplished with various masking techniques or by splitting off the flow until the desired composition is present.

Disposed adjacent to a bottom surface of the substrate, a temperature controlled heating block 128 is operable for sintering the array of electrode or electrolyte materials to remove any binders and/or carrier materials prior to SOFC assembly and evaluation. In the case of ceramics a high temperature may be desired. Disposed between the heating block 128 and the x-y stage 126, an insulator 130 protects the x-y stage 126 from heat. The heating block 12 includes a temperature control device. Sintering of the metal salt mixtures may take place in-situ with spraying, however, in most cases, post-spray sintering may be necessary.

The methods and systems of the present invention are used to investigate materials for both electrode and electrolyte materials for SOFCs. The plurality of materials 104 forms the gradient array of electrode or electrolyte materials on the substrate 106. Thus, the plurality of materials 104 may form, for example, a discrete array of electrode materials separated by electrolyte material, a continuous array of electrode materials, a discrete array of electrolyte materials, a continuous array of electrolyte materials, or any combination thereof.

Electrode and electrolyte mixtures are selected by characterizing properties of interest of the mixtures, or by characterizing a property of interest of a component, such as zirconium ($Zr^{4+}$), yttrium ($Y^{3+}$), nickel ($Ni^{2+}$), scandium ($Sc^{2+}$), etc. In one example, the property is detected over a period of time and as a percentage of mixture composition, such that a variation in the property is observed and detected and the rate of change of variation of the property is observed and detected. A property of interest is any property that affects the performance of electrode and electrode-electrolyte combinations.

For electrolyte investigations, a maskless approach may be employed. In this embodiment, a decomposable substrate allows for the formation of a gradient solid. Sputtering a metal on one side of the ceramic substrate creates a common electrode, sputtering an array of discrete metal contacts on the other side, using the mask 112, isolates a compositional spot between the two electrodes for electrochemical characterization. For cathode materials, a similar approach may be performed by spraying either discrete or continuous gradient mixtures on an anode-electrolyte substrate. The anode provides a general common for each cell while a metal contact may be sputtered onto the cathode materials using the mask 112. Such a design allows for the electrochemical evaluation of the materials under fuel containing conditions.

The plurality of materials 104 comprises SOFC components, the individual substances that are deposited onto the substrate 106. The components may act upon one another to produce a particular material. Components may react directly with each other or with an external energy source such as thermal radiation. An additional material or a chemical substance present in the substrate 106 or added to the components may also act upon the components. The components form layers, blends, mixtures or combinations thereof. The plurality of materials 104 may comprise, for example, a plurality of materials suitable for providing predetermined metal ions, metal cations, combinations of metal ions, and/or combinations of metal cations to the surface of the substrate 106, such as metal oxides, metal carbonates, metal salts and the like. The plurality of materials 104 may comprise metal solutions that contain metals for bulk and dopant purposes, along with organic binders or polymers for structural variation. Other suitable materials known to those of ordinary skill in the art may also be used for both the electrodes and the electrolytes. The plurality of materials 104 may further include binders and/or carrier materials to enhance the coating and/or infiltrating processes.

The components or combination of components that have been deposited on to a predefined region of the substrate 104 comprise a layer, blend or mixture of components in the form of a gradient array. Each component in the mixture may be independently varied. A mixture comprises two or more substances. The resulting materials of the gradient array are screened for specific properties or characteristics to determine their relative performance.

In another exemplary embodiment, an array of electroactive materials may be formed as described above. However, before sintering and before or after compositional doping, a chemical agent may be added to a spot of interest in an attempt to influence change in the microstructure of that spot. For example, an agent may be added that, after sintering, allows for variable control of porosity or packing density. This allows for both compositional and microstructural control on a small scale. Relationships between microstructure, composition, and material performance may thus be discovered and optimized rapidly.

The systems and methods of the present invention describe the creation of a multi-composition cell, which allows for the rapid study of cathode and anode materials suitable for use in SOFCs. By spraying an anode of a uniform material with a common cathode material, different regions of the multi-composition cell may be measured and regions evaluated for performance. Performance to composition may determined rapidly using a multi-channel or multi-electrode analyzer.

Preferably, the system for the evaluation of an array of electrode or electrolyte materials for use in SOFCs also includes a testing device operably coupled to each of a plurality of regions of the substrate 106 via one or more leads, probes, sensors, or the like, referred to herein as one or more sampling mechanisms. The testing device gathers data from the one or more sampling mechanisms and, optionally, in combination with a computer, evaluates and compares the relative performance of each mixture of the gradient array. The testing device and the computer may comprise a multi-channel electrochemical workstation capable of sampling each member of the array in series or in parallel. For the evaluation of electrode materials for use in SOFCs, electrical resistance, over-potential, polarization current or the like may be measured, evaluated and compared. Each of the individual materials may be screened or interrogated for the same material characteristic. For example, over-potential may be measured using a constant-current approach. Polarization current may be measured using a constant-voltage approach. For the evaluation of electrolyte materials for use in SOFCs, ionic resistance, open circuit voltage, or the like may be measured, evaluated, and compared using an alternating-current ("AC") impedance analyzer, a potentiastat or the like. Preferably, with respect to the measurement of ionic resistance, it is measured using electrochemical impedance spectroscopy at a single frequency. Other measurement, evaluation and comparison tools and techniques related to the performance of electrodes, electrolytes, and SOFCs are known to those of ordinary skill in the art and may be implemented in conjunction with the systems and methods of the present invention. Such tools and techniques may also be implemented in conjunction with an environmental control device operable for isolating the array of electrodes, electrolytes, or SOFCs from the surrounding environment. Once screened, the individual materials may be ranked or otherwise compared relative to each other with respect to a material characteristic under investigation.

One or more microprocessors may be employed for automating and controlling every aspect of the LC systems of the present invention, including: the LC instrument 108, mixing tube 120, injection system 122, mass flow controller 124, ultrasonic nebulizer 110, shutter 118, mask 112, x-y stage 126, temperature controlled heating block 128, testing equipment, sensors, compositional gradients, temperature gradients, sample selection, sample preparation and any other operation or system component.

It is apparent that there have been provided, in accordance with the systems and methods of the present invention, high-throughput techniques for the fabrication and evaluation of arrays of electrode and electrolyte materials for use in solid oxide fuel cells. Although the systems and methods of the present invention have been described with reference to preferred embodiments and examples thereof, other embodiments and examples may perform similar functions and/or achieve similar results. All such equivalent embodiments and examples are within the spirit and scope of the present invention and are intended to be covered by the following claims.

What is claimed is:

1. A method for the fabrication and evaluation of a gradient mixture of solid oxide fuel cell components, the method comprising:

simultaneously and controllably supplying solid oxide fuel cell component materials from a sample library using an auto-sampler to form a multi-compositional mixture;

controlling the flow of the multi-compositional mixture using a mass flow controller;

spraying the flow onto a substrate using a delivery apparatus;

creating a compositional gradient array; and evaluating the performance of the multi-compositional mixture for use in solid oxide fuel cells.

2. The method of claim 1, wherein the multi-compositional mixture comprises electrode materials, electrolyte materials, metals, non-metals, soluble metal salts, organic binders and polymers.

3. The method of claim 1, further comprising creating discrete or continuous gradient compositions using a mask and a shutter, wherein the shutter is operable for selectively allowing/preventing the multi-compositional mixture from being sprayed onto the substrate by opening/closing.

4. The method of claim 3, further comprising sintering the substrate and multi-compositional mixture after the multi-compositional mixture is applied to the substrate.

5. The method of claim 4, further comprising controlling an x-y motion of the substrate and the delivery apparatus using a programmable x-y motion stage.

6. The method of claim 1, wherein the delivery apparatus comprises an ultrasonic nebulizer, an ultrasonic nebulizer for flame deposition, or a sprayer.

7. The method of claim 5, further comprising controlling the functions of the auto-sampler, mass flow controller, delivery apparatus and x-y motion stage using a programmable general purpose processor.

8. A method for the fabrication and evaluation of electrode and electrolyte material performance for solid oxide fuel cells, the method comprising:

providing a library of samples comprising electrode materials, electrolyte materials, metals, non-metals, soluble metal salts, organic binders, polymers, and any other components used to produce the solid oxide fuel cells;

continuously and controllably supplying desired amounts of the samples to a liquid chromatography system where a multi-compositional mixture is formed;

serially loading the multi-compositional mixture into a common sprayer;

serially and distributively spraying the multi-compositional mixture onto a surface of a substrate using a spraying apparatus;

forming a discrete or continuous gradient array of the mixture reacted on the substrate; and evaluating the performance of the mixture for use in solid oxide fuel cells.

9. The method of claim 8, further comprising movably positioning the substrate and the spraying apparatus using an x-y motion stage.

10. The method of claim 8, wherein the spraying apparatus comprises an ultrasonic nebulizer, an ultrasonic nebulizer for flame deposition, or a sprayer.

11. The method of claim 8, further comprising forming the discrete or continuous gradient array of the mixture using a mask and a shutter, wherein the shutter selectively allows/prevents the mixture from being sprayed onto the substrate by opening/closing.

12. The method of claim 8, further comprising sintering the substrate and multi-compositional mixture after the multi-compositional mixture is applied to the substrate.

* * * * *